(12) United States Patent
Mongomery et al.

(10) Patent No.: US 7,250,137 B2
(45) Date of Patent: Jul. 31, 2007

(54) APPARATUS AND PROCESS FOR CONDITIONING MAMMALIAN BLOOD

(75) Inventors: Sonya Mongomery, Mississauga (CA); Jeff Dayman, Waterloo (CA); Allen Muirhead, Mississauga (CA); Paul Moore, Mississauga (CA); Taras Worona, Mississauga (CA); Simon Treadwell, Mississauga (CA); Murray Voakes, Mississauga (CA); Thomas Porter, Toronto (CA); Carlton Chong, Toronto (CA); Liung Sen Liao, Toronto (CA); Duncan Newman, Toronto (CA)

(73) Assignee: Vasogen Ireland Limited, Clare (IE)

( * ) Notice: Subject to any disclaimer, the term of this patent is extended or adjusted under 35 U.S.C. 154(b) by 0 days.

(21) Appl. No.: 11/294,384

(22) Filed: Dec. 6, 2005

(65) Prior Publication Data
US 2006/0073069 A1 Apr. 6, 2006

Related U.S. Application Data

(62) Division of application No. 10/827,329, filed on Apr. 20, 2004, now Pat. No. 7,128,873, which is a division of application No. 09/662,706, filed on Sep. 15, 2000, now Pat. No. 6,736,788.

(60) Provisional application No. 60/154,215, filed on Sep. 16, 1999.

(51) Int. Cl.
*A61M 1/00* (2006.01)
*A61M 37/00* (2006.01)
*C02F 1/44* (2006.01)

(52) U.S. Cl. .................. 422/44; 422/45; 604/4.01; 604/6.14; 604/6.15

(58) Field of Classification Search ............... 604/4.01, 604/5.04, 6.08, 6.14, 6.15, 23–25, 403, 416, 604/405, 406; 206/363–366; 222/129, 132, 222/145.5; 321/31, 31.1; 422/44–48; 137/583, 137/590, 602, 896
See application file for complete search history.

(56) References Cited

U.S. PATENT DOCUMENTS 3,946,731 A 3/1976 Lichtenstein
4,578,056 A 3/1986 King et al.

(Continued)

FOREIGN PATENT DOCUMENTS

DE 1 068 428 11/1959

(Continued)

*Primary Examiner*—Tatyana Zalukaeva
*Assistant Examiner*—Leslie R. Deak
(74) *Attorney, Agent, or Firm*—Buchanan Ingersoll & Rooney PC

(57) ABSTRACT

An apparatus for conditioning mammalian blood for subsequent use in a medical procedure includes a cabinet having a secure environment and a door providing the only access to the environment. An input system transports a blood charge from a source to the cabinet and a flask is removably contained in the secure environment and coupled to the charge input system to receive the charge. Stressors are coupled to the cabinet and positioned for operation to create a conditioned charge in the flask. An output system is coupled to the flask and includes a receiver for the conditioned charge. The apparatus includes an automated control system operable upon closing the door to lock the door and to then condition the charge, and to then cause the charge to move from the flask to the receiver.

19 Claims, 4 Drawing Sheets

U.S. PATENT DOCUMENTS

| | | |
|---|---|---|
| 4,596,547 A | 6/1986 | Troutner |
| 4,968,483 A * | 11/1990 | Muller et al. ............... 422/45 |
| 5,030,200 A | 7/1991 | Judy et al. |
| 5,037,390 A | 8/1991 | Raines et al. |
| 5,052,382 A | 10/1991 | Wainwright |
| 5,104,373 A | 4/1992 | Davidner et al. |
| 5,254,080 A * | 10/1993 | Lindsay ................. 604/6.15 |
| 5,466,229 A | 11/1995 | Elson et al. |
| 5,540,898 A | 7/1996 | Davidson |
| 5,591,457 A | 1/1997 | Bolton |
| 5,593,893 A | 1/1997 | Kobashi et al. |
| 5,628,727 A | 5/1997 | Hakky et al. |
| 5,687,717 A | 11/1997 | Halpern et al. |
| 5,800,721 A * | 9/1998 | McBride ................ 210/806 |
| 5,834,030 A | 11/1998 | Bolton |
| 5,935,092 A | 8/1999 | Sun et al. |
| 5,980,954 A | 11/1999 | Bolton |
| 6,113,566 A | 9/2000 | Schleicher |
| 6,142,971 A | 11/2000 | Daoud et al. |
| 6,146,354 A | 11/2000 | Beil |
| 6,190,609 B1 * | 2/2001 | Chapman et al. ........... 422/24 |
| 6,268,119 B1 | 7/2001 | Sumita et al. |
| 6,544,162 B1 * | 4/2003 | Van Wie et al. ............. 494/37 |
| 6,613,280 B2 | 9/2003 | Myrick et al. |
| 6,719,715 B2 | 4/2004 | Newman et al. |
| 6,802,892 B2 | 10/2004 | Newman et al. |

FOREIGN PATENT DOCUMENTS

| | | |
|---|---|---|
| DE | 24 56 932 | 6/1976 |
| DE | 35 11 159 A1 | 10/1986 |
| DE | 43 23 295 C1 | 2/1995 |

* cited by examiner

APPARATUS AND PROCESS FOR CONDITIONING MAMMALIAN BLOOD

This application is a divisional application of application Ser. No. 10/827,329, filed on Apr. 20, 2004 now U.S. Pat. No. 7,128,873, which is a divisional of application Ser. No. 09/662,706, filed on Sep. 15, 2000, now U.S. Pat. No. 6,736,788, which claims the benefit of 35 U.S.C. § 119(e) of U.S. Provisional Application No. 60/154,215, filed Sep. 16, 1999.

FIELD OF THE INVENTION

This invention relates to a process and apparatus for treating mammalian blood by preparing a blood charge, and treating the charge to prepare conditioned charge in preparation for injecting the conditioned charge into a patient as part of a medical procedure.

BACKGROUND OF THE INVENTION

Various treatments have been proposed for the treatment of mammalian blood ex vivo to condition the blood in some way before injecting the blood into a patient. Some procedures take blood from a patient, condition the blood, and then return the blood to the same patient continuously. These procedures contrast with procedures which require that the blood be taken from the patient to be treated as a batch and then returned to the patient. In batch processes there is the possibility that the blood will be given to the wrong patient as well as the dangers inherent in transferring blood from one location to another. Also, batch treatments are potentially hazardous because of the risk of blood contamination during the process of conditioning the blood and also because of the potential for infecting the operator accidentally.

The present invention is directed at the problems inherent in the batch process of treating mammalian blood.

A blood treatment process using batch treatment techniques involves three main steps. Firstly, the blood is sourced either from a donor or from a patient, who will also be the patient receiving the conditioned blood. The blood may be mixed with an anticoagulant and the blood charge must then be transferred to apparatus used to condition the charge. Finally, the conditioned charge has to be collected and prepared for injection into the patient. These steps involve the use of needles (sharps), tubing, valves, syringes and ancillary parts and connectors. At every stage it is important to minimize risk so that the charge is moved and treated without contamination, and so that none of the charge comes into contact with the operator running the procedure.

Accordingly, it is among the objects of the present invention to provide a process and apparatus for receiving a blood charge, conditioning the charge, and preparing the conditioned charge for injecting into a patient while minimizing the risk of contamination and spillage.

It is also an object of the invention to provide a disposable flask assembly for use in a machine designed to condition a charge in the flask assembly and prepare the conditioned charge ready for injection.

SUMMARY OF THE INVENTION

In one of its aspects, the invention provides apparatus for conditioning mammalian blood for subsequent use in a medical procedure. The apparatus includes a cabinet having a secure environment and a door providing the only access to the environment. An input system is provided for transporting a blood charge from a source to the cabinet and a flask is removably contained in the secure environment and coupled to the charge input system to receive the charge. Stressors are coupled to the cabinet and positioned for operation to create a conditioned charge in the flask. An output system is coupled to the flask and includes a receiver for the conditioned charge.

The apparatus includes an automated control system operable upon closing the door to lock the door and to then condition the charge, and to then cause the charge to move from the flask to the receiver. As a result, a charge from the input system is conditioned and delivered to the receiver, the door is then unlocked and the conditioned charge is ready to be removed and used to complete the medical procedure.

In another of its aspects, the invention provides a cabinet for use in conditioning mammalian blood for subsequent use in a medical procedure. A blood charge is conditioned in a flask and the cabinet has a front defining a front recess and a top defining a depression adjacent to the front recess. A door is hinged for movement between an open position and a closed position in which the front recess and the depression are covered by the door to create a secure environment, and a lock is coupled to the cabinet and to the door to lock the door in the closed position. A cavity extends downwardly from the top depression within the secure environment, and is adapted to receive the flask. A control system is coupled to the door lock to sense the condition of the door to establish that the flask is securely positioned in the cabinet and that the door is locked before the charge is conditioned. The charge can then be conditioned in the flask securely within the cabinet.

In yet another of its aspects, the invention provides a cabinet for use in conditioning mammalian blood for subsequent use in a medical procedure. A blood charge is conditioned in a flask and the cabinet has a front, a top, and a door hinged for movement between an open position and a closed position in which at least a portion of the front and a portion of the top are covered by the door to create a secure environment. A lock is coupled to the cabinet and to the door to lock the door in the closed position, and a cavity extends downwardly from the top wall within the secure environment to receive the flask. A control system is coupled to the door lock to sense the condition of the door to establish that the flask is in the secure environment within the cabinet, and that the door is locked before the charge is conditioned.

In still another of its aspects, the invention provides a flask assembly for use in apparatus having a cabinet made to receive the flask assembly for conditioning mammalian blood. The flask assembly includes a flask in the form of an envelope defining a substantially enclosed volume, and including a top and a bottom. The top has an access opening and an outlet, and a connector assembly is coupled to the top of the flask. A probe extends from the connector assembly, through the access opening and has a top end and a leading end. The probe is sealed in the access opening and defines an input lumen for transporting a blood charge to the bottom of the flask, an output lumen for transporting conditioned charge from the bottom of the flask out of the flask, and a gas lumen for feeding gas into the flask to condition the charge when a charge is in the flask. The connector assembly includes outlet tubing coupled to the outlet to lead spent gas out of the flask, and inlet tubing coupled to the gas lumen. A pair of gas connectors is coupled to the platform and connected to the respective gas inlet tubing and to the gas outlet tubing to make gas connections when the flask assembly is mounted in the apparatus. As a result, when the flask is engaged in the cabinet, the gas connections engage a gas supply system for conditioning the charge in the flask before removing the conditioned charge.

In yet another aspect of the invention, a process is provided of treating mammalian blood in a blood charge to provide a conditioned charge for giving to a patient in a medical procedure. The process includes the steps of providing an automatic apparatus for treating the blood charge to create the conditioned charge, and for presenting the conditioned charge ready for use. The apparatus has a secure environment, a door controlling access to the environment, a flask, and stressors arranged to operate on a charge in the flask in the controlled environment. The blood charge is transported into the secure environment through thermoplastic inlet tubing for deposit in the flask, and the tubing is then sealed and severed. Next the part of the inlet tubing outside the secure environment is removed and the operation of the automatic apparatus is initiated so that the stressors will operate on the charge for a predetermined period, thereby stressing the charge in the flask while maintaining the secure environment. The apparatus is then given time to transport the conditioned charge from the flask to a receiver, and the door is opened to provide access to the receiver for use to give the conditioned charge to the patient.

BRIEF DESCRIPTION OF THE DRAWINGS

The invention, in all its aspects, will be more fully understood with reference to the following drawings taken in combination with the description. In the drawings.

DESCRIPTION OF THE PREFERRED EMBODIMENT(S)

Figure 1:
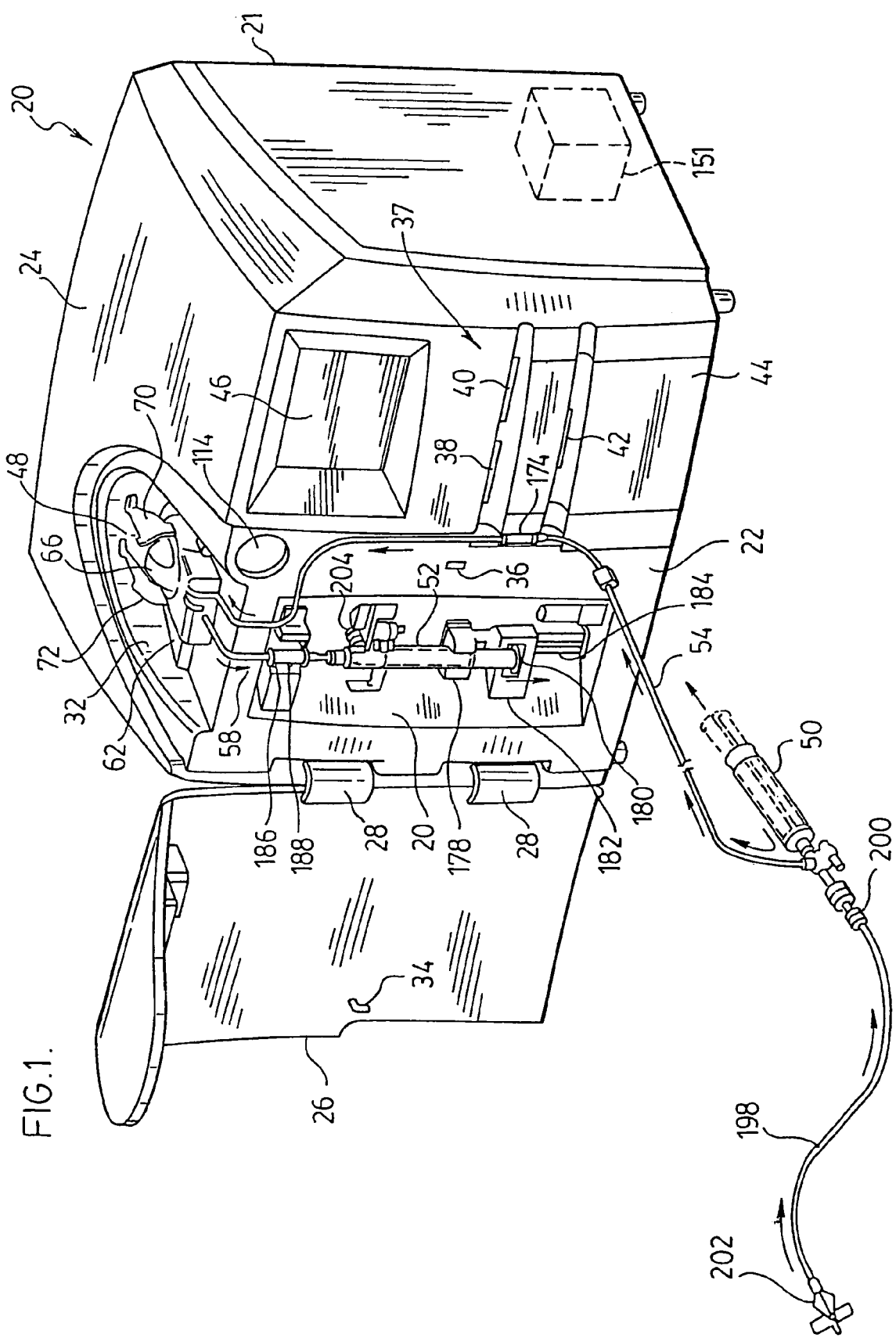
FIG. 1 is an isometric view of apparatus used in practicing a process of conditioning blood charges in accordance with a preferred embodiment of the invention and including a cabinet.

The invention will be described initially with reference to FIG. 1, which shows the apparatus generally, and then more detail will be given with reference to further drawings. As seen in FIG. 1, apparatus, designated generally by the numeral 20, includes a cabinet 21 having a front 22 and an inclined top 24. A hinged door 26 is attached to the cabinet 21 to one side of the front to move about vertical hinges 28 between an open position shown in FIG. 1, and a closed position (not shown) where it covers a front recess 30 and a top depression 32. The door is equipped with a locking bar 34 which engages in a recess 36 where it can be retained to hold the door in the closed and locked position to create a secure environment inside the cabinet 21.

As will become evident from further description, the apparatus 20 is shown after it has been prepared for use to condition a blood charge in a accordance with the process of the invention. The apparatus 20 will be described in this position to provide a general understanding of the apparatus and then in more detail with reference to the process and subsequent Figures.

The cabinet 21 is designed to be secure while the charge is being conditioned. As will be explained. The apparatus 20 includes an identification system 37 so that the apparatus 20 can be used by an operator only after a patient has been designated and identified by the apparatus by way of a discrete smart card (not shown) which has to be inserted by the patient in a first slot 38. A second smart card is inserted by the operator in a second slot 40. The patient keeps the patient's smart card so that the apparatus can be used only by the operator in the presence of the patient until the apparatus is ready to treat another charge. The smart cards can be used to store data developed during operation of the apparatus and can become a permanent record of the procedure.

A third slot 42 in a printer door 44 will produce a printed record of the treatment as required.

The operator controls the apparatus using a graphical display terminal (GDT) 46 having a touch screen interface pad overlaid on the GDT. The GDT serves to interrogate the operator to ensure that every required step is completed in the required sequence. Errors and instructions are also available on the GDT.

Figure 2:
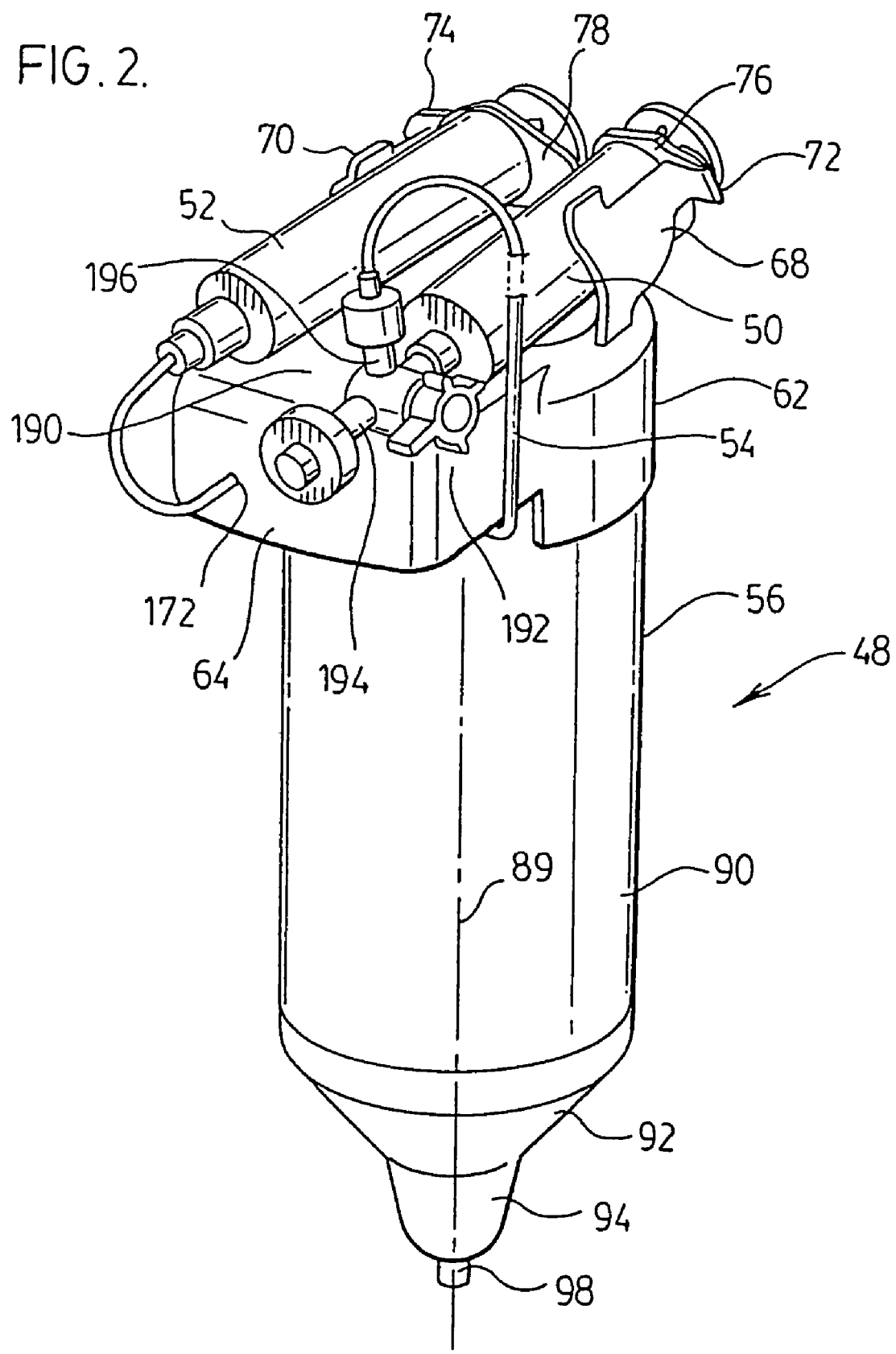
FIG. 2 is an isometric view of a disposable flask assembly adapted for use with the apparatus.

As mentioned, the door 26 can be moved into a locked and closed position to cover the front recess 30 and the top depression 32. In the position shown in FIG. 1, a sterile flask assembly, designated generally by the numeral 48, has been lowered into the cabinet such that part of the assembly 48 can be seen projecting upwardly into the depression 32. An input syringe 50, and an output syringe 52 have been removed from the assembly 48 ready for use. The input syringe 50 is used to source a charge and pass the charge through thermoplastic inlet tubing 54 to a flask 56 which can be seen in FIG. 2. After treatment in the flask 56, the conditioned charge is drawn through outlet tubing 58 from the flask 56 into the syringe 52 by an actuator 60, as will be explained later. For the moment it is sufficient to understand that there are three stages to the treatment. Firstly, the charge is sourced and passed by syringe 50 to the flask 56 (FIG. 2). Next, treatment takes place in the flask 56 and then the conditioned charge is drawn automatically from the flask into the output syringe 52 ready for injection into the patient. All of these steps are controlled by the apparatus 20 in such a way that there is a limited risk of contamination of the charge, and of exposing the charge to the operator. Further the patient is identified by the identification system 37 in such a way that if the charge is sourced from the patient for subsequent return to that patient, the treated charge will be available only when the patient presents his/her smart card to thereby ensure that the right patient gets the charge.

Reference is next made to FIG. 2 to describe the main features of the flask assembly 48 as it would appear in a sterile condition ready for placement in the cabinet 21 (FIG. 1). The flask assembly 48 will be supplied in a sterile container which will also include most of the items needed for the procedure. These will include needles, tubing, gauze etc. as is commonly done in medical procedures requiring sterile items for the procedure.

The assembly 48 is made up of two main parts, namely the flask 56 and a connector assembly 62 which serves to carry components used in the treatment procedure. The assembly 48 is shown as it would be placed in the cabinet 21 (FIG. 1), with the input syringe 50 and output syringe 52 mounted side-by-side on the connector assembly 62. The assembly 62 is shown from the back as opposed to from the front in FIG.

1. It will be seen that the connector assembly includes an overhanging portion 64 which will meet parts of the apparatus contained in the cabinet 21 when the flask assembly 48 is lowered downwardly into the cabinet 21. As will be described, electrical and gas connections are made automatically when the assembly 48 moves into its final position in the cabinet 21. Also, the overhanging portion 64 provides clearance under the portion 64 to allow the inlet tubing 54 to be fed from the input syringe 50 to a supply probe 65 (FIGS. 3 and 4).

The syringes 50 and 52 are conveniently stored on the connector assembly 62 between a central shaped mound 66 (FIG. 1) and respective locators 68 and 70 which are sufficiently flexible to allow the syringes to be engaged and held in place. Further location is provided by respective channel portions 72, 74 which receive respective flanges 76, 78 on the syringes 50 and 52. This interengagement locates the syringes 50, 52 longitudinally but does not interfere with vertical removal of the syringes 50, 52.

Figure 3:
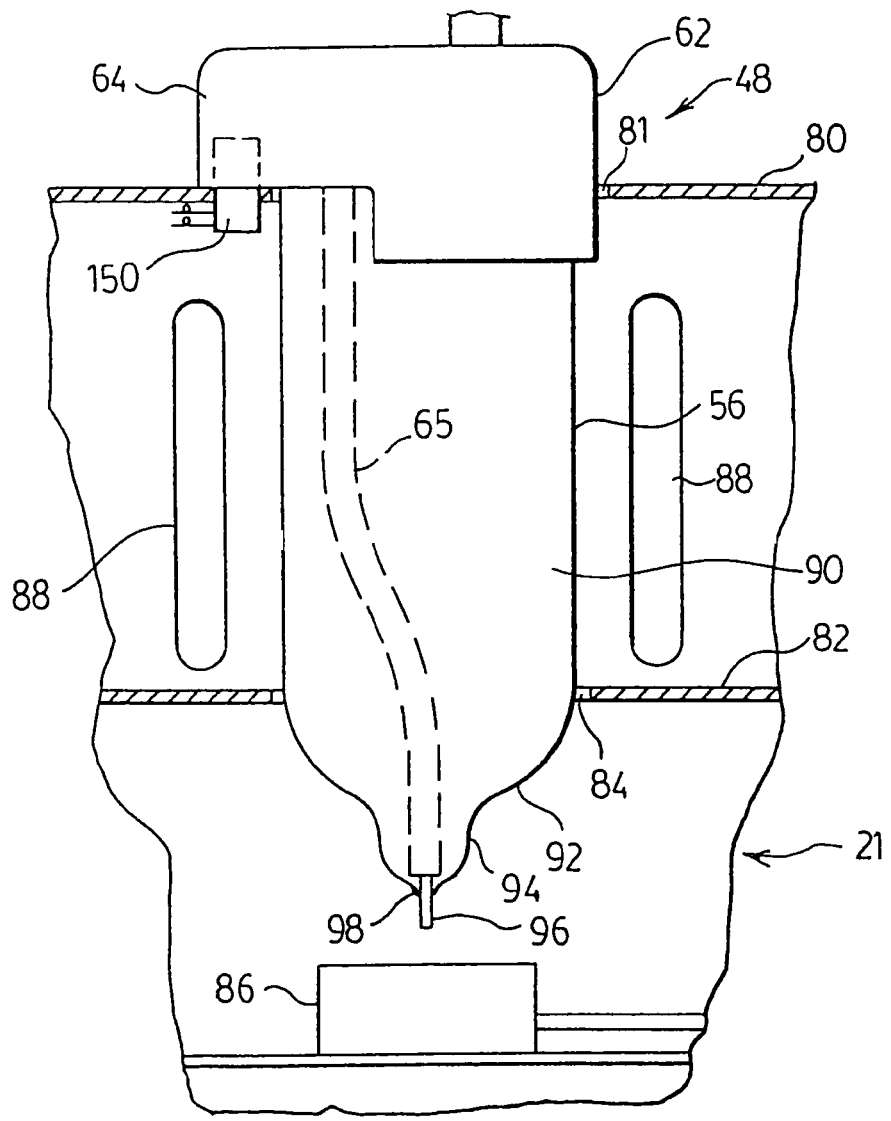
FIG. 3 is a schematic side view of the flask assembly in position in the cabinet and showing structure used to condition the charge.
Figure 4:
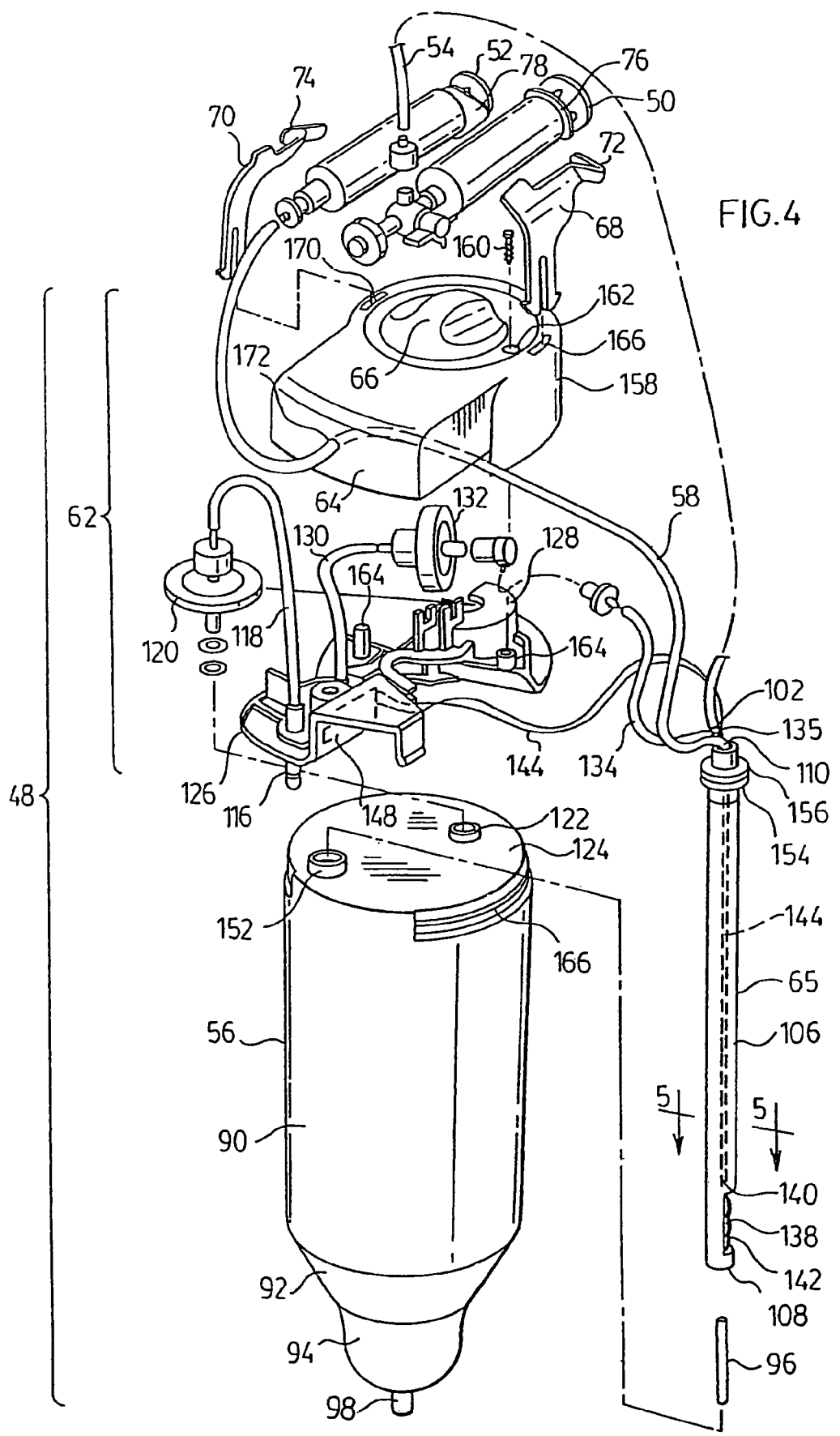
FIG. 4 is an exploded isometric view of the flask assembly showing details of the construction.

As seen in FIG. 3, the flask assembly 48 is located in the cabinet 21 by a shelf 80 having an opening 81 for the flask 56, and below the shelf, a locator 82 having an opening 84 which is also proportioned to receive the flask 56 loosely. The connector assembly 62 rests on the shelf 80 about the opening 84 to locate the flask assembly 48 vertically and in proper relationship with two of the stressors to which the charge is to be subjected. One of these stressors is heat supplied by an infrared (IR) heater 86, another is ultraviolet (UV) light provided by an UV radiator 88 positioned about the flask 52. Also, in the process of lowering the flask assembly 48 in the cabinet 21, the overhanging portion 64 of the connector assembly 62 brings electrical connectors and gas supply connections together as will be explained after describing FIG. 4.

FIG. 3 also shows the shape of the flask 56. It extends about a longitudinal axis 89 and has a generally cylindrical main portion 90. A transitional portion 92 extends from the portion 90 to a cup 94 proportioned to receive about 12 ccs of charge from the input syringe 50 FIG. 1).

Figure 5:
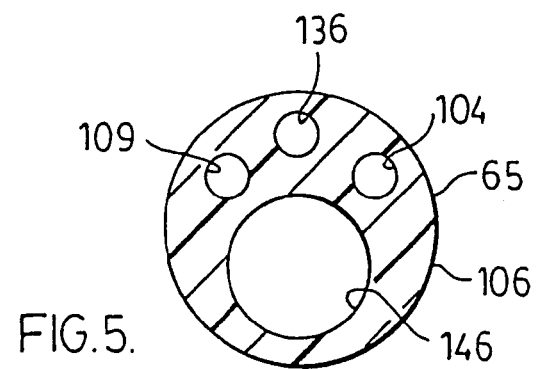
FIG. 5 (drawn adjacent FIG. 3) is a sectional view on line 5-5 of FIG. 4 and drawn to a larger scale.

The supply probe 65 will be described more fully with reference to FIG. 5. For the moment it is sufficient to understand that the function of the probe 65 is to supply charge to and remove conditioned charge from the flask 56. Also, a mixture of ozone and oxygen is fed through a lumen in the probe 65 and a temperature sensor is provided in the probe 65. Heat from the IR heater 86 causes the charge to heat and that together with the gas supply, causes the charge to bubble and fill the flask 56. The large surface area so formed is then subject to UV light from the radiator 88. These stressors are used to condition the charge before it is delivered by the apparatus to the output syringe 52, (FIG. 1).

The probe 65 is located centrally in the cup 94 by a solid extension 96 at the end of the probe 65. The extension fits closely inside a cylindrical socket 98 formed in the bottom of the flask 58, and extending from the cup 94. The extension 96 is placed in the socket 98 during assembly and the socket is crimped from the outside to retain the extension 96 in the socket 98 and to thereby secure the supply probe 65 in the flask 56

The flask 56 is essentially an envelope made by blow moulding a parazon of low density polyethylene (LDPE) and has an internal volume that is about 70 times that of the charge. The walls are translucent to allow penetration of the UV light stressor.

Reference is next made to FIG. 4 which is an exploded view of the flask assembly 48 with the syringes 50 and 52 included. This assembly includes parts of several systems. Firstly an input system made of parts associated with receiving a charge and placing it in the flask 56 ready for conditioning it. Next, an output system is made up of parts related to extracting the conditioned charge from the flask 56, and lastly, parts related to gas supply and recovery system.

The charge is received in the input syringe 50 which is connected by the thermoplastic tubing 54 to an elbow 102 forming part of the probe 65. This elbow leads to an intake lumen 104 formed in an extruded main body 106 which can be seen in the cross-sectional view, FIG. 5. This view is taken on line 5-5 of FIG. 4. The intake lumen 104 extends to a leading end 108 of the probe adjacent the extension 96. Consequently, the charge can be fed into the cup 94 of the flask 56 by actuating the syringe 50 to move the charge through the inlet tubing 54, through the elbow 102, and then via the lumen 104 into the cup 94.

The second set of parts is related to the removing the conditioned charge. The syringe 52 is the prime mover so that when it is actuated, the charge is drawn from the cup 94 into a return lumen 109 at the end 108 of the probe 65. The charge then passes through the lumen 109 leaving via an elbow 110 which in turn leads to outlet tubing 58 and to the syringe 52.

The third set of parts mentioned above relate to a gas supply and recovery system creates ozone from oxygen and supplies and removes an ozone/oxygen mixture. Oxygen from a replaceable oxygen supply cartridge 114 passes through an ozone generator (not shown) built into the cabinet 21 (FIG. 1). Connections to the flask assembly 48 are made automatically when the assembly 48 is lowered into the cabinet as described previously. To facilitate these connections, a pair of nipples 116 (one of which can be seen in FIG. 4) engage in suitable receptors (not shown) in the cabinet. The nipple that can be seen in FIG. 4 is connected to gas exhaust tubing 118 which leads to an in-line filter 120 having fittings for sealably connecting to a cup 122 formed in a top 124 of the flask 56. The exhaust gas from the process is carried by these parts to an exhaust system as is conventional when using ozone.

The connector assembly 62 includes a moulded platform 126 shaped to carry the various components. As indicated in FIG. 4, the outlet filter 120 is normally mounted in a holder 128 shaped to receive the disk-shaped filter 120.

The connection to the gas supply is made using the hidden nipple 116 which supplies gas to a gas inlet tubing 130. In turn, the tubing 130 directs gas to an in-line filter 132 which is associated with standard connections to send the gas to a gas supply tubing 134. The filter 132 is arranged to engage in a support 137 formed in the platform 126, and an elbow 135 on the probe 65 is connected to the tubing 134 to lead the gas to a gas lumen 136 in the extruded probe main body 106. This lumen, like the intake lumen 104 and return lumen 109, leads to the end 108 of the main body which will be submerged in charge when the charge is entered through the lumen 104.

The probe 65 also locates a temperature sensor 138 exposed near the end 108 through a side opening 140 cut into the side of the main body 106. A sterile sleeve 142 of very thin filmic plastics material encloses the sensor, but because the sleeve 142 is thin, there is a rapid temperature transfer to allow the sensor 138 to respond quickly to changes in temperature.

The sensor 138 is connected by conductive ribbon 144 which extends through a larger lumen 146 (FIG. 5) in the probe 46, and then to a connector 148 mounted on the platform 126. This connector 148 is adapted to engage a corresponding sliding connector 150 (FIG. 3) mounted in the shelf 80 of the cabinet 21. The connector 150 cooperates with the connector 148 to connect the temperature sensor 138 to a control system indicated generally at 151 in FIG. 1 and contained in the cabinet 21 (FIG. 1).

The assembled supply probe 65 is passed through a receiver 152 formed in the top 124 of the flask 56, and the extension 96 at the leading end of the probe 65 is manoeuvred into the socket 98 under the cup 94 of the flask 56. The socket 98 is then crimped from the outside sufficiently to positively locate the extension, and hence the probe, relative to the flask 56. At the same time a seal 154 under a collar 156 on the outer end of the main body 106 is brought to bear against the receiver 152 and held in compression while the socket 98 is crimped. As a result the probe is sealed in the flask with a gas tight seal.

After this assembly, the platform 126 and the parts mounted on the platform are attached to a cover 158. This is done by the use of two self-tapping screws 160 (one of which is shown) which pass through openings 162 and engage in respective bosses 164 formed in the platform 126.

The sub-assembly of the platform 126 and the cover 158 is then attached to the flask 56 using snap-fitting structure 166 formed on the flask 56 and on the cover 158. This structure is discontinuous around the flask so that there is only one way to attach the sub-assembly to the flask 56 thereby ensuring that the parts line up correctly to engage the cup 122 on the flask 56 and to provide the necessary clearance under the overhanging portion 64 of the connector assembly 62 for the various tubing, gas connections and electrical connections.

The flask assembly 48 then receives the syringe locators 68 and 70 which snap into respective slots 168, 170 formed in the top of the cover 158. The outlet tubing 58 is then fed through an opening 172 at the back of the cover 158 and attached to the syringe 52. Similarly, the inlet tubing 54 is attached to the syringe 50 and the syringes are engaged on the cover 158 to be held in place (as previously described) by the combinations of the mound 66 with the respective locators 68 and 70.

The completed flask assembly 48 is sterilized and packaged for use as mentioned earlier.

The main structural details have been described. Some details have been omitted because they are more readily described with reference to the process of conditioning the charge using the apparatus. That process will now be described and those parts of the structure that have not been mentioned will be included in this part of the description.

The process in general is designed to source suitable mammalian blood either by using compatible blood or by using blood taken from a patient who is to receive the treated blood. This process will be described for the latter case but is not to be limited to that case.

The apparatus must be readied for use by placing the operator's smart card in the slot 40. A patient's smart card comes with the package containing the flask assembly 48 and is given to the patient for the patient to place the card in the slot 38. The GDT 46 then proceeds to present instruction, error messages, and comments as the procedure progresses.

Once this is done, the door 26 is unlocked by the control circuit, and a new flask assembly 46 is removed from its sterile package and lowered into a cavity in the cabinet to take up the position shown in FIG. 1 and further illustrated in FIG. 3. At this point the syringes 50, 52 are in place on the connector assembly 62.

Next the input syringe 50 is lifted from its position on the connector assembly 62 and placed conveniently with the inlet tubing 54 passing through a heat sealing device 174 which is attached to the cabinet 21 for use to seal and sever the inlet tubing 54 as will be explained. The inlet tubing 54 has a locator 176 mounted on the tubing to position the inlet tubing 54 in the device 174.

The output syringe 52 is then removed in similar fashion and placed vertically as shown in FIG. 1. The syringe 52 is located in a fixed mount 178 using the flange 78 and a syringe operator 180 extends downwardly and is engaged in an actuator 182 which can be driven along a slide 184 by a motor and drive (not shown) in the cabinet. This operation will be described with reference to removing a conditioned charge.

The outlet tubing 58 associated with the syringe 52 is led through a second heat sealing device 186, and a locator 188 on the tubing 58 positions the outlet tubing in the device 186. This device 186 will be used after the conditioned charge is drawn into the syringe 52, as will be explained.

A message on the GDT 46 (FIG. 1) reminds the operator to close the door 26 and the door lock bar 34 is engaged. The control system 151 (FIG. 1) activates the door so that the cabinet can be opened only by using the two smart cards. Consequently the smart card carried by the patient is necessary so that no one other than the patient can cooperate with the operator to get into the cabinet 21. The patient's smart card is preferably attached to the patient's wrist in a semi-permanent fashion using a suitable band of the type commonly used in hospitals.

The input syringe 50 is still in the condition shown in FIG. 2. A T-connector 190 includes a valve controlled by a selector 192 which connects the body of the syringe to either an in-line port 194, or a side port 196 at right angles to the axis of the body. The inlet tubing 54 is attached to the port 196 and the port 194 is available.

A needle (not shown) is attached to port 194 and about 2 ccs of an anti coagulant (preferably sodium citrate) is drawn into the syringe. The needle is discarded into a sharps container and then a tubing assembly 198 (FIG. 1) is attached to the in-line port 194. This assembly 198 includes a one-way valve 200, to avoid back flow, and at its leading end an angel wing collector set 202 is ready for engagement into the patient to collect blood. The collector set is used to draw 10 ccs of blood into the syringe 50 where it is mixed with the sodium citrate by rocking the syringe gently to create a blood charge for treatment in the process according to the invention.

Next, the selector 192 on the T-connector 190 is operated to connect the body of the syringe 50 with the side port 196 leaving the tubing assembly attached but inoperable. The syringe 50 is then inverted (i.e. placed with the T-connector uppermost) and about 3 to 4 ccs of sterile air are drawn from the flask 56 into the syringe. The syringe 50 is then again inverted so that the air is above the charge and the syringe is then operated to drive the charge through the inlet tubing 54 and into the flask 56 driven by the air in the syringe. As a result the inlet tubing is cleaned out as the air follows the charge.

It is now time to discard the input syringe 50 and associated parts. Before this can be done, the syringe 50 has to be separated from the cabinet 21 to which it is connected by the inlet tubing 54. This is achieved by operating the heat sealing device 186 which seals and severs the tubing under the influence of heat.

Once this step is completed the input syringe 50 and attached parts are discarded.

It should be noted that the door 26 (FIG. 1) has not been opened during this procedure and that the charge of blood and sodium citrate has been received in the cup 94 of the flask 56 (FIG. 3). It should be noted that although the process is too condition blood, to be accurate the process treats blood as the prime part of a charge which also contains an anticoagulent, (or any other additive). Consequently the term "charge" is used to describe a batch made up of blood and at least one additive. However if circumstances arise in which blood can be treated alone, such use is within the scope of the term because mammalian blood continues to be the subject of the treatment and it is not intended to exclude such an interpretation.

The next stage of the process can now begin. The control system 151 in the cabinet 21 takes over and starts the IR heater 86 (FIG. 3) to elevate the temperature of the charge. This is one example of a process know generally as "stressing" the charge and the IR radiator is known as a "stressor". The temperature is elevated to about 42.5° C. and is controlled from a reading originating with the temperature sensor 138. Once the selected temperature has been reached, the control system activates a second stressor. An ozone generator sends an oxygen/ozone mixture into the flask 56 through the probe 65 as described earlier. Also, the UV light source 88 (third stressor) is activated so that the heated charge is simultaneously stressed by the ozone/oxygen mixture and by the UV light simultaneously for about 3 minutes. The bubbled charge fills the flask and is then allowed to settle and cool for about 6 minutes so that bubbles in the charge will tend to settle.

At this point the charge has been conditioned and the GDT 46 (FIG. 1) will respond to the control system to give the operator a message that the smart cards will be needed to withdraw the conditioned charge. However the door 26 (FIG. 1) will not open until the charge is available in the output syringe 52 even if the cards are inserted at this stage. On the other hand, if the charge is in the syringe (as will be explained) and ready for removal, the door 26 will remain closed unless the cards are inserted.

Next the apparatus will commence the step of moving the charge from the flask 56 (FIG. 3) to the output syringe 52 (FIG. 1). This is done automatically by the actuator 182 seen in FIG. 1, which draws the operator 180 downwardly. A knocker 204 is then driven to tap the syringe at a rate of about 1 Hertz to break any resident bubbles. The knocker consists of an impact tool 205 mounted in the recess 30 of the cabinet, and driven to strike the syringe 52 gently thereby deflecting the syringe sideways to store energy in a coil spring 207 positioned on the opposite side of the syringe from the tool 205. The energy in the spring then causes the spring to rebound thereby pushing the syringe back into contact with the impact tool 305 ready for the next impact. The frequency can be varied and will to some extent depend on the geometry and mass of the parts. However, it has been found that a frequency of 1 Hertz with a spring having a spring rate of between about 0.1 to 5N° provides good results.

Next the actuator 182 is operated to express some of the contents of the syringe 52 back into the outlet tubing 58 until there remains a volume of 9 to 10 ccs of conditioned charge. A sensor (not shown) in the heat sealing device 186 tells the control system in the cabinet 21 that the system is ready to seal the outlet tubing 58 in similar fashion to the seal made on the inlet tubing 54 as previously described.

The process has now reached a critical point. If the patient has not inserted the patient's smart cad by now, the apparatus will wait only for a predetermined time (usually about 20 minutes) before aborting the process. If the process is to be aborted, a message will appear on the GDT 46 (FIG. 1) and the control system will cause the actuator 180 to drive the syringe operator 182 so that the conditioned charge is returned to the flask 56 before shutting down the process. Once this is done the operator can open the door 26 using only the operator's card so that the flask 56 and its contents can be discarded to ready the apparatus 20 for a new process.

If the patient presents the card in time, the respective smart cards are inserted into the slots 38, 40 and the heat sealer 186 will seal and sever the tubing 58, the door 26 will open, and the output syringe 52 is then available for removal from the cabinet 21. However, before this is done, the patient must be prepared for the injection of about 8 to 9 ccs of conditioned charge. Firstly, the patient is anaesthetized in the Gluteus Maximus muscle using a suitable needle and performing the standard procedure for ensuring that the needle has not been inserted into a vein. Next, the anaesthetic syringe is removed and the needle is left in the patient. The output syringe 52 is then taken to the anaesthetic needle and after discarding the remaining tubing 58 from the heat sealing operation, the output syringe 52 is attached to the anaesthetic needle and the conditioned charge is fed into the patient slowly. After this procedure, the output syringe and attached needle are discarded.

The apparatus can then be prepared for the next procedure by removing the remains of the flask assembly 48.

It will now be evident that the process can be used to treat mammalian blood in a blood charge to provide a conditioned charge for giving to a patient in a medical procedure. In general the process includes the steps of providing an automatic apparatus for treating the blood charge to create the conditioned charge, and for presenting the conditioned charge ready for use. The apparatus has a secure environment, a door controlling access to the environment, a flask, and stressors arranged to operate on a charge in the flask in the controlled environment. The blood charge is transported into the secure environment through thermoplastic inlet tubing for deposit in the flask, and the tubing is then sealed and severed. Next the part of the inlet tubing outside the secure environment is removed and the operation of the automatic apparatus is initiated so that the stressors will operate on the charge for a predetermined period, thereby stressing the charge in the flask while maintaining the secure environment. The apparatus is then given time to transport the conditioned charge from the flask to a receiver, and the door is opened to provide access to the receiver for use to give the conditioned charge to the patient.

Improved control can be provided by the preferred use of smart cards, as explained, and by the use of thermoplastic tubing and heat sealers to ensure that the secure environment is maintained. Also, the process can be enhanced by use of the knocker to reduce the time needed to dissipate the bubbles in the conditioned charge It will be appreciated that the described embodiments of the apparatus, and of the process associated with the apparatus, can be varied within the scope of the claims and that such variations are within the scope of the invention.

The invention claimed is:

1. A flask assembly for use in apparatus having a cabinet made to receive the flask assembly for conditioning mammalian blood, the flask assembly including:
   a flask in the form of an envelope defining a substantially enclosed volume and including a top and a bottom, the top having an access opening and an outlet;
   a connector assembly coupled to said top of the flask;
   a probe extending from the connector assembly, through the access opening and having a top end and a leading end, the probe being sealed in the access opening and defining an input lumen for transporting a charge to the bottom of the flask, an output lumen for transporting conditioned charge from the bottom of the flask out of the flask, and a gas lumen for feeding gas into the flask to condition the charge when a charge is in the flask;

the connector assembly including outlet tubing coupled to said outlet to lead spent gas out of the flask, and inlet tubing coupled to the gas lumen;

a pair of gas connectors coupled to a platform and connected to the respective gas inlet tubing and to the gas outlet tubing to make gas connections when the flask assembly is mounted in the apparatus, whereby as the flask is engaged in the cabinet the gas connectors engage a gas supply system for conditioning said charge in the flask before removing the conditioned charge;

the probe including a further lumen containing a temperature probe for monitoring the temperature of the charge, the temperature probe being located near the leading end of the probe; and said further lumen ends at a side opening in the probe, and the temperature probe being positioned in the opening for better thermal conductivity from the charge to the temperature sensor.

2. A flask assembly as claimed in claim 1 in which said enclosed volume is in the order of about 70 times the volume of the charge to be entered into the flask.

3. A flask assembly as claimed in claim 1 in which the flask is of low density polyethylene.

4. A flask assembly as claimed in claim 1 in which the platform includes an overhanging portion extending outwardly from said top, and in which the gas connectors are mounted on the overhanging portion and in which the gas supply system includes fittings adapted to be mounted on the cabinet for engagement with the gas connectors when the flask is engaged in the cabinet.

5. A flask assembly as claimed in claim 1 and further including a cover attached to the platform to contain the platform and present a cleaner appearance.

6. A flask assembly as claimed in claim 5 in which the cover is attached to the flask.

7. A flask assembly as claimed in claim 6 in which the cover is a snap fit on the flask, and in which the cover and flask are arranged so that the cover fits on the flask with the outlet tubing aligned with the outlet in said top.

8. A flask assembly as claimed in claim 1 and further including in-line filters in the gas inlet tubing and in the gas outlet tubing, the in-line filters being mounted on the platform.

9. A flask assembly as claimed in claim 1 in which the flask defines an upper cylindrical portion and a smaller lower cup at the bottom of the flask, the cup being proportioned to receive the charge, and in which the leading end of the probe is contained close to said bottom.

10. A flask assembly as claimed in claim 1 and further including a an extension engaged in the leading end of said further lumen and projecting downwardly, and in which the flask includes a socket at the leading end shaped to receive the extension to locate the leading end of the probe relative to the flask.

11. A flask assembly as claimed in claim 1 in which: the flask defines an upper cylindrical portion and a smaller lower cup at the bottom of the flask, the cup being proportioned to receive the charge, and in which the leading end of the probe is contained close to said bottom; and in which the flask assembly further includes an extension engaged in the leading end of said further lumen and projecting downwardly, and in which the flask includes a socket at the leading end shaped to receive the extension to locate the leading end of the probe relative to the cup.

12. A flask assembly as claimed in claim 1 in which the platform includes an overhanging portion extending outwardly from said top, and electrical contacts mounted on the overhanging portion for engagement automatically with suitable fittings adapted to be mounted on the cabinet when the flask is engaged in the cabinet.

13. A flask assembly as claimed in claim 1 and further comprising input and output syringes releasably mounted on the connector assembly, the input syringe being connected to the input tubing and the outlet syringe being connected to the output tubing.

14. A flask assembly for use in apparatus having a cabinet made to receive the flask assembly for conditioning mammalian blood, the flask assembly including:

a flask in the form of an envelope defining a substantially enclosed volume and including a top and a bottom, the top having an access opening and an outlet;

a connector assembly coupled to said top of the flask;

a probe extending from the connector assembly, through the access opening and having a top end and a leading end, the probe being sealed in the access opening and defining an input lumen for transporting the charge to the bottom of the flask, an output lumen for transporting conditioned charge from the bottom of the flask out of the flask, and a gas lumen for feeding gas into the flask to condition the charge when a charge is in the flask;

the connector assembly including outlet tubing coupled to said outlet to lead spent gas out of the flask, and inlet tubing coupled to the gas lumen;

a pair of gas connectors coupled to a platform and connected to the respective gas inlet tubing and to the gas outlet tubing to make gas connections when the flask assembly is mounted in the apparatus, whereby as the flask is engaged in the cabinet the gas connectors engage a gas supply system for conditioning said charge in the flask before removing the conditioned charge; and the probe including a further lumen containing a temperature probe for monitoring the temperature of the charge, the temperature probe being located near the leading end of the probe, and the platform including an overhanging portion extending outwardly from said top, and electrical contacts mounted on the overhanging portion for engagement automatically with suitable fittings adapted to be mounted on the cabinet when the flask is engaged in the cabinet.

15. A flask assembly as claimed in claim 14 in which: the flask defines an upper cylindrical portion and a smaller lower cup at the bottom of the flask, the cup being proportioned to receive the charge, and in which the leading end of the probe is contained close to said bottom; and in which the flask assembly further includes an extension engaged in the leading end of said further lumen and projecting downwardly, and in which the flask includes a socket at the leading end shaped to receive the extension to locate the leading end of the probe relative to the cup.

16. A flask assembly as claimed in claim 14 in which said further lumen ends at a side opening in the probe, and in which the temperature probe is positioned in the opening for better thermal conductivity from the charge to the temperature sensor.

17. A flask assembly for use in apparatus having a cabinet made to receive the flask assembly for conditioning mammalian blood, the flask assembly including:
- a flask in the form of an envelope defining a substantially enclosed volume and including a top and a bottom, the top having an access opening and an outlet;
- a connector assembly coupled to said top of the flask;
- a probe extending from the connector assembly, through the access opening and having a top end and a leading end, the probe being sealed in the access opening and defining an input lumen for transporting the charge to the bottom of the flask, an output lumen for transporting conditioned charge from the bottom of the flask out of the flask, and a gas lumen for feeding gas into the flask to condition the charge when a charge is in the flask;
- the connector assembly including outlet tubing coupled to said outlet to lead spent gas out of the flask, and inlet tubing coupled to the gas lumen;
- a pair of gas connectors coupled to a platform and connected to the respective gas inlet tubing and to the gas outlet tubing to make gas connections when the flask assembly is mounted in the apparatus, whereby as the flask is engaged in the cabinet the gas connectors engage a gas supply system for conditioning said charge in the flask before removing the conditioned charge; and
- input and output syringes releasably mounted on the connector assembly, the input syringe being connected to the input tubing and the outlet syringe being connected to the output tubing.

18. A flask assembly as claimed in claim 17 in which the probe includes a further lumen containing a temperature probe for monitoring the temperature of the charge, the temperature probe being located near the leading end of the probe.

19. A flask assembly as claimed in claim 18 in which said further lumen ends at a side opening in the probe, and in which the temperature probe is positioned in the opening for better thermal conductivity from the charge to the temperature sensor.

* * * * *